(12) United States Patent
Li

(10) Patent No.: US 11,801,377 B2
(45) Date of Patent: Oct. 31, 2023

(54) CENTRIFUGAL BLOOD PUMP

(71) Applicant: Chinabridge (Shenzhen) Medical Technology Co., Ltd, Guangdong (CN)

(72) Inventor: Yijiang Li, Shenzhen (CN)

(73) Assignee: Chinabridge (Shenzhen) Medical Technology Co., Ltd, Shenzhen (CN)

(*) Notice: Subject to any disclaimer, the term of this patent is extended or adjusted under 35 U.S.C. 154(b) by 62 days.

(21) Appl. No.: 17/141,210

(22) Filed: Jan. 4, 2021

(65) Prior Publication Data
US 2021/0220635 A1 Jul. 22, 2021

(30) Foreign Application Priority Data
Jan. 21, 2020 (CN) .......................... 202010068244.9

(51) Int. Cl.
| | | |
|---|---|---|
| *A61M 60/38* | (2021.01) | |
| *A61M 60/419* | (2021.01) | |
| *A61M 60/806* | (2021.01) | |
| *A61M 60/814* | (2021.01) | |
| *A61M 60/205* | (2021.01) | |

(Continued)

(52) U.S. Cl.
CPC .......... *A61M 60/38* (2021.01); *A61M 60/205* (2021.01); *A61M 60/419* (2021.01); *A61M 60/806* (2021.01); *A61M 60/814* (2021.01); *F04D 7/045* (2013.01); *F04D 29/043* (2013.01); *F04D 29/24* (2013.01); *F04D 29/426* (2013.01)

(58) Field of Classification Search
CPC ........ A61M 2205/3606; A61M 60/205; A61M 60/232; A61M 60/825; A61M 60/419; A61M 60/38; A61M 60/806; A61M 60/814; F04D 25/062; F04D 25/0626; F04D 29/0467; F04D 29/061; F04D 13/026; F04D 13/0633
See application file for complete search history.

(56) References Cited

U.S. PATENT DOCUMENTS

| | | | | |
|---|---|---|---|---|
| 6,015,434 | A | * | 1/2000 | Yamane ................ A61M 60/82 623/3.13 |
| 6,234,772 | B1 | * | 5/2001 | Wampler .............. F04D 29/047 417/423.1 |

(Continued)

FOREIGN PATENT DOCUMENTS

| | | |
|---|---|---|
| CN | 1483939 A | 3/2004 |
| CN | 2754637 Y | 2/2006 |

(Continued)

OTHER PUBLICATIONS

First Examination Notice dated Sep. 7, 2020, in counterpart Chinese Patent Application No. 202010068244.9, filed on Jan. 21, 2020, and English translation of the portion containing the substantive examination (16 pages).

*Primary Examiner* — Christopher R Legendre
(74) *Attorney, Agent, or Firm* — Maier & Maier, PLLC

(57) ABSTRACT

A pump head includes a casing including a blood inlet configured to receive a flow of a blood and a blood outlet configured to allow the blood to flow out of the casing. The pump head also includes a shaft disposed in the casing. The pump head also includes a magnetic structure mounted onto the shaft. The pump head further includes an impeller having an open structure and mounted to an exterior surface of the magnetic structure through an opening provided at the open structure.

9 Claims, 10 Drawing Sheets

(51) Int. Cl.
*F04D 7/04* (2006.01)
*F04D 29/043* (2006.01)
*F04D 29/24* (2006.01)
*F04D 29/42* (2006.01)

(56) References Cited

U.S. PATENT DOCUMENTS

| | | | | |
|---|---|---|---|---|
| 6,254,359 | B1 * | 7/2001 | Aber | A61M 60/237 |
| | | | | 417/423.12 |
| 6,716,157 | B2 * | 4/2004 | Goldowsky | A61M 60/122 |
| | | | | 600/16 |
| 6,986,640 | B2 * | 1/2006 | Laing | F04D 29/426 |
| | | | | 415/126 |
| 7,871,566 | B2 * | 1/2011 | Strauss | F04D 7/04 |
| | | | | 604/4.01 |
| 8,672,611 | B2 * | 3/2014 | LaRose | F04D 13/0666 |
| | | | | 415/104 |
| 9,616,157 | B2 * | 4/2017 | Akdis | F04D 29/048 |
| 10,828,408 | B2 * | 11/2020 | Granegger | A61M 60/82 |
| 2006/0222533 | A1 * | 10/2006 | Reeves | A61M 1/3659 |
| | | | | 417/423.1 |

FOREIGN PATENT DOCUMENTS

| | | | |
|---|---|---|---|
| CN | 102348474 A | 3/2014 | |
| CN | 104826183 A | 8/2015 | |
| CN | 107050542 A | 8/2017 | |
| CN | 107405435 A | 11/2017 | |
| CN | 107469168 A | 12/2017 | |
| CN | 107477023 A | 12/2017 | |
| CN | 108601873 A | 9/2018 | |
| CN | 110191727 A | 8/2019 | |
| WO | WO-0038816 A1 * | 7/2000 | A61M 1/1036 |

* cited by examiner

CENTRIFUGAL BLOOD PUMP

CROSS-REFERENCE TO RELATED APPLICATION

This application claims priority to Chinese Patent Application No. 202010068244.9, filed on Jan. 21, 2020. The entire contents of the above-mentioned application are incorporated herein by reference.

TECHNICAL FIELD

The present disclosure generally relates to the technical field of medical devices and, more specifically, to a pump head, a pump including the pump head, and an extracorporeal membrane oxygenation ("ECMO") device including the pump. The pump including the pump head may be used in an artificial heart.

BACKGROUND TECHNOLOGY

Extracorporeal membrane oxygenation ("ECMO") is an important technology for providing life support to seriously ill patients who have severe cardiopulmonary function failure. An ECMO device primarily includes a pump for an artificial heart, an oxygenator, oxygen supply tubings (or conduits), and blood circulation tubings (or conduits).

A pump head of a dynamic pump is used along with the dynamic pump for extracorporeal blood circulation or blood circulation assistance in a heart surgery. Various issues have been observed in pump heads of conventional technologies in clinical applications. The issues associated with the pump heads of conventional technologies may include, for example, an inclination to form blood clot (or emblolus), destruction of blood cells, complex precharge exhaust processes, high blood flow resistance, etc. In conventional technologies, Chinese Patent Application No. CN201510272655.9 discloses a blood flow guiding device including a centrifugal maglev artificial heart pump, which resolves the issue of blood flow hysteresis to a certain degree. But the solution provided by this patent document attempts to reduce or eliminate the blood flow hysteresis and blood clotting (or embolism) primarily from the perspective of flow guiding. The solution provided in this patent document still cannot solve the issues related to destruction of the blood cells in the blood, damage to the blood, and blood clot formation.

SUMMARY OF THE DISCLOSURE

One objective of the present disclosure is to provide a concept for mitigating or addressing disadvantages and issues of conventional technical solutions.

Another objective of the present disclosure is to provide a novel pump head for a pump that may be used in an artificial heart, a pump having the pump head, and an ECMO device including the pump having the pump head.

According to a first aspect of the present disclosure, the above and other objectives are realized based on the pump head that may be used in an artificial heart. The pump head includes a volute casing with a blood inlet and a blood outlet.

In some embodiments, a shaft may be disposed at a center location inside the volute casing. In some embodiments, the shaft may be fixed to the volute casing (e.g., non-rotatable). For example, the shaft may be fixed to a lower portion of the volute casing and may extend inside the volute casing along a central axis of the volute casing. In some embodiments, a magnetic structure may be sleeve-fit onto the shaft. In some embodiments, a conical impeller having an open structure may be mounted to an exterior surface of the magnetic structure. When the magnetic structure rotates, the magnetic structure may drive the conical impeller to rotate.

In some embodiments, a first gap may exist between the shaft and the magnetic structure. When the magnetic structure drives the conical impeller to rotate, a portion of the blood may flow from a bottom of the volute casing upwardly through the first gap toward a top of the volute casing. At least partially due to the buoyant force generated by the upward blood flow, the conical impeller (along with the magnetic structure to which the conical impeller is coupled) may suspend in the blood.

In some embodiments, a plurality of vanes may be disposed at an exterior surface of the conical impeller. The plurality of vanes may include a plurality of alternately disposed first vanes and second vanes that may be spaced apart from one another. Top portions of the first vanes may be connected through a first bowl-shaped structure having a downward opening 401.

In some embodiments, an end of the shaft may include a second bowl-shaped structure having an upward opening 402. In some embodiments, a spherical structure may be disposed (e.g., embedded) between the first bowl-shaped structure and the second bowl-shaped structure. When the magnetic structure drives the conical impeller to rotate, a second gap may exist between the spherical structure and the first bowl-shaped structure and the second bowl-shaped structure. During an operation of the pump, the second gap may be filled with blood.

In some embodiments, the first vanes and the second vanes may be configured to tilt toward a same side at a predetermined angle. In some embodiments, heights of the first vanes may be greater than heights of the second vanes.

In some embodiments, the magnetic structure may include a mounting shaft having a hollow body. An annular wheel structure may be disposed at a bottom portion of the mounting shaft. A diameter of the annular wheel structure may be substantially the same as a diameter of an opening at a bottom portion of the conical impeller.

In some embodiments, a plurality of mounting grooves may be provided at a surface of the annular wheel structure. The mounting grooves may be spaced apart from one another. In some embodiments, magnetic elements may be mounted in the mounting grooves.

In some embodiments, an outer diameter of the mounting shaft may be substantially the same as a diameter of an opening provided at a top portion of the conical impeller.

In some embodiments, the spherical structure may be a ceramic ball bearing.

In some embodiments, the blood inlet may be configured to be perpendicular to a cross-sectional plane of the volute casing. The blood outlet may be tangent to the cross-sectional plane of the volute casing at the periphery of the volute casing.

Compared with the conventional technologies, the volute pump head configured for use in an artificial heart according to the present disclosure can be used along with a dynamic pump of the artificial heart. To address the deficiencies and disadvantages of the conventional technologies, the systems and devices of the present disclosure can provide a reasonable extracorporeal blood circulation environment. The technical solutions provided by the present disclosure can be used in portable emergency rescue devices such as ECMO devices. The volume of the pump head of the present disclosure is small, which can effectively reduce the precharge amount. The disclosed pump head includes a conical impeller having an open structure, which makes it easier to exhaust gas bubbles from the blood. The heights and the tilting design of the first vanes and the second vanes may be configured to be advantageous for thorough flushing and for effectively reducing blood clot formation and destruction of blood cells. The design of the conical impeller and the shaft disposed inside the volute casing can effectively reduce heat generation, reduce the blood clot formation, and avoid destruction of the blood cells.

According to a second aspect of the present disclosure, the present disclosure also provides a pump, which may be used for an artificial heart. The pump may include the volute pump head configured for use in the artificial heart according to any of the technical solutions disclosed herein.

Compared with the conventional technologies, the advantages of the pump provided by the present disclosure are similar to the advantages of the volute pump head configured for use in the artificial heart as disclosed herein, which are not repeated.

According to a third aspect of the present disclosure, the present disclosure also provides an ECMO device. The ECMO device includes the pump configured for the artificial heart according to any of the technical solutions disclosed herein.

Compared with the conventional technologies, the advantages of the ECMO device provided by the present disclosure are similar to the advantages of the volute pump head configured for use in the artificial heart as provided herein, which are not repeated.

It should be understood that the above brief descriptions and the following detailed descriptions are illustrative descriptions and explanations, which should not be construed as limiting the scope of the protection of the present disclosure.

BRIEF DESCRIPTION OF THE DRAWINGS

With reference to the accompanying drawings, the objectives, functions, and advantages of the present disclosure will be explained through the following descriptions of various embodiments of the present disclosure. In the drawings.

DETAILED DESCRIPTION

Figure 1:
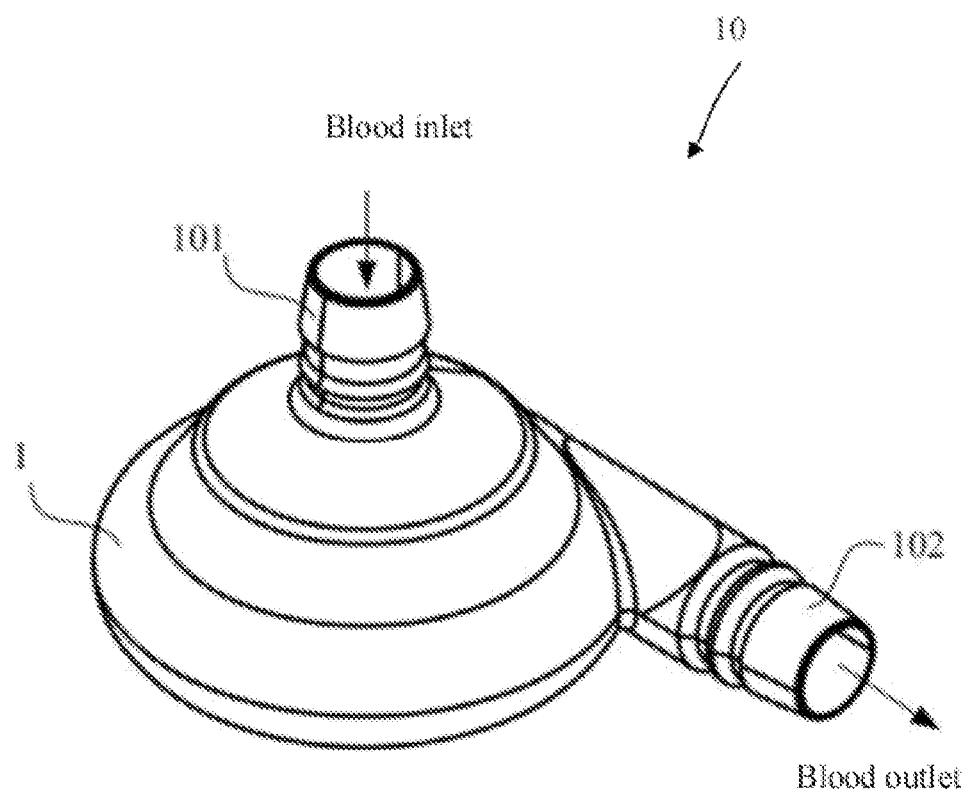
FIG. 1 schematically illustrates a perspective view of an overall structure of a volute pump head configured for use in an artificial heart, according to an embodiment of the present disclosure.

The objectives and functions of the present disclosure, as well as the methods for achieving these objectives and functions, will be explained in detail with reference to illustrative embodiments shown in the drawings. The present disclosure is not limited by the illustrative embodiments disclosed herein. The objectives and the functions of the present disclosure may be realized through other different manners. The descriptions are intended to assist a person having ordinary skills in the art in achieving comprehensive understanding of the specific implementations of the technical solutions provided by the present disclosure.

In order to solve issues related to the pump head configured for use in an artificial heart in the conventional technologies, such as the inclination to form blood clots, destruction of the blood cells, complex precharge exhaust processes, high blood flow resistance, etc., the present disclosure provides the following technical solutions. The technical solutions are described and explained with reference to the illustrative embodiments shown in the accompanying drawings.

Figure 10:
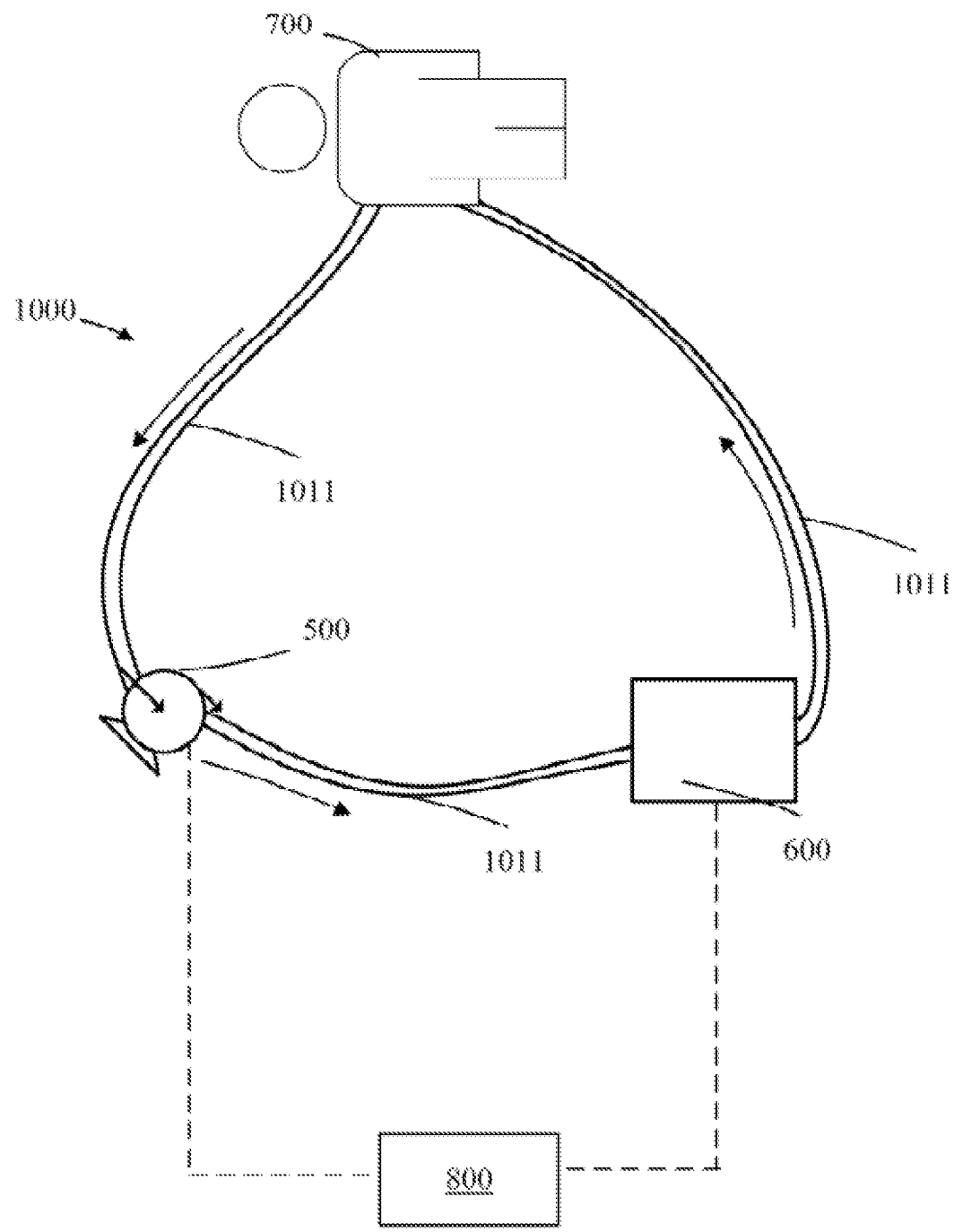
FIG. 10 schematically illustrates an ECMO device, according to an embodiment of the present disclosure.

FIG. 1 schematically illustrates a perspective view of an overall structure of a pump head 10, which may be configured for use in an artificial heart. According to an embodiment, the pump head 10 may be a part of a centrifugal blood pump. The pump head 10 may include a volute casing 1. Thus, the pump head 10 may be referred to as a volute pump head. The volute casing 1 may include a blood inlet 101 configured to receive a flow of a blood, and a blood outlet 102 configured to allow the blood to flow out of the volute casing 1. It is understood that the volute casing is used as an example. In other embodiments, the casing 1 may not be a volute casing. In an emergency surgery, the blood of a human body flows into the inner space of the volute casing 1 through the blood inlet 101, and flows out of the volute casing 1 through the blood outlet 102. The blood flowing out from the pump head 10 may be directed into an oxygenator (an example of which is shown in FIG. 10), where blood oxygenation is performed. The oxygenated blood flowing out of the oxygenator may flow into the human body (e.g., a heart of the human body).

According to some embodiments of the present disclosure, the blood inlet 101 may be perpendicular to a cross-sectional plane of the volute casing 1. The blood inlet 101 may be disposed at an upper portion of the volute casing 1. The blood outlet 102 may be disposed at a lower portion of the volute casing 1. The blood outlet 102 may be disposed at a circumferential portion along a direction tangent to the cross-sectional plane of the volute casing 1. That is, the blood outlet 102 may be tangent to the cross-sectional plane of the volute casing 1 at the periphery of the volute casing 1. As shown in FIG. 1, in some embodiments, the blood inlet 101 and the blood outlet 102 may be perpendicular to one another. The cross-sectional plane of the volute casing 1 refers to a plane in which a cross section of the volute casing 1 is located. In some embodiments, the blood inlet 101 is disposed at a center location of the volute casing 1. For example, an extension of the blood inlet 101 may pass through a center of the cross section of the volute casing 1. In some embodiments, the cross-sectional plane of the volute casing 1 may have a circular shape or a near circular shape. In some embodiments, the cross-sectional plane of the volute casing 1 may have other suitable shapes, such as an oval shape. Each of the blood inlet 101 and the blood outlet 102 may be in a form of a tube. The blood inlet 101 may be a tube protruding from the upper portion of the volute casing 1. The blood outlet 102 may be a tube extending tangent to a circumferential portion of the lower portion of the volute casing 1.

Figure 2:
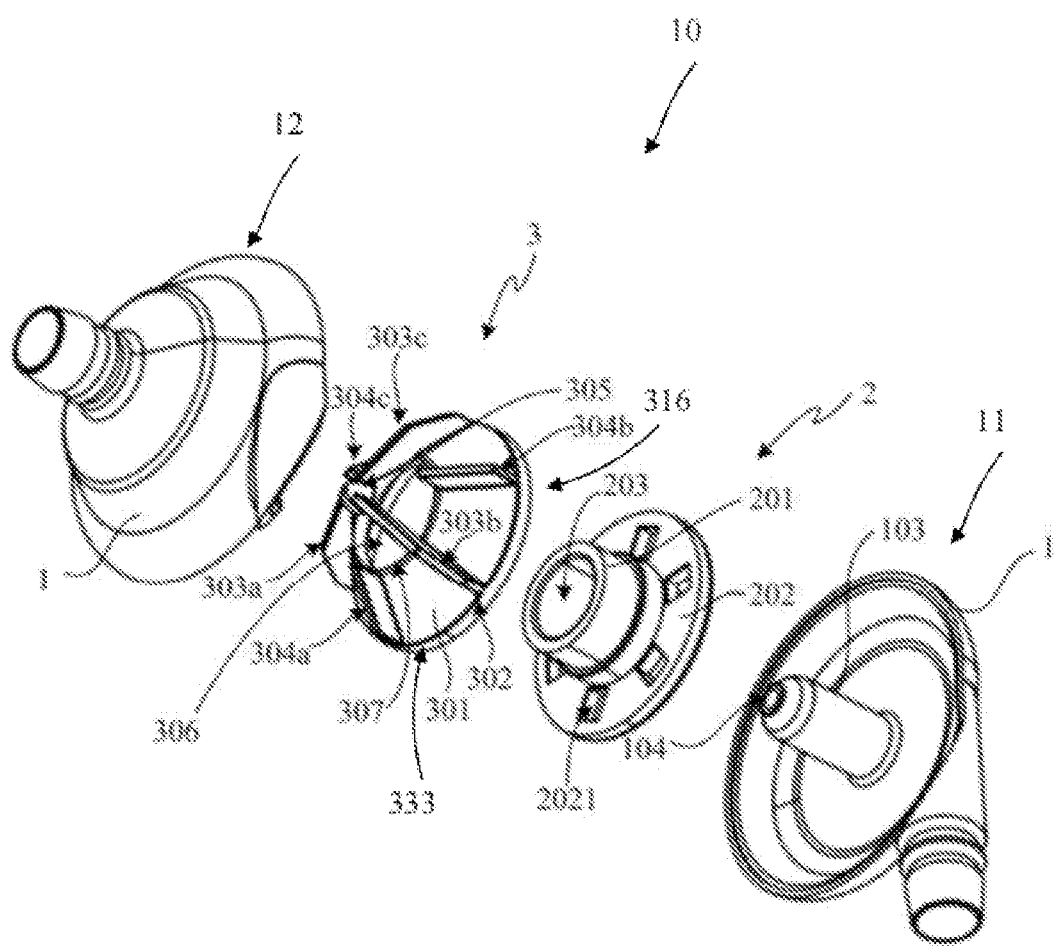
FIG. 2 schematically illustrates an exploded view of the structure of the volute pump head configured for use in the artificial heart, according to an embodiment of the present disclosure.
Figure 3:
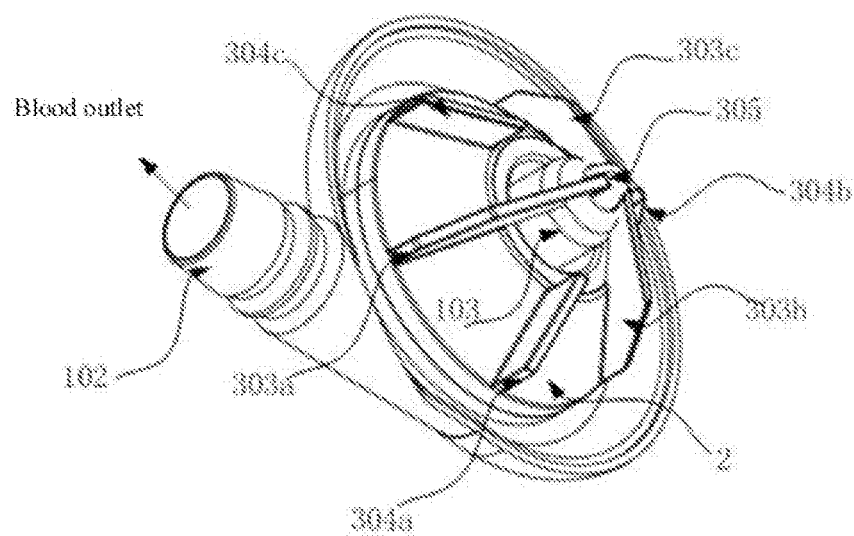
FIG. 3 schematically illustrate a perspective view of the structure of the volute pump head configured for use in the artificial heart with a portion of a volute casing removed, according to an embodiment of the present disclosure.

As shown in FIG. 2 and FIG. 3, a shaft 103, a magnetic structure 2, and an impeller 3 having an open structure 333 may be disposed inside the volute casing 1. In some embodiments, as shown in FIG. 2, the open structure 333 may have a cone shape. It is understood that the shape of the open structure 333 is not limited to the cone shape. The open structure 333 may have any suitable shape other than a cone shape. For discussion purposes, the impeller 3 may be referred to as a conical impeller 3. It is understood that the pump head 10 may be made of any suitable materials that can provide a long service life suitable for use in an artificial heart.

Figure 5:
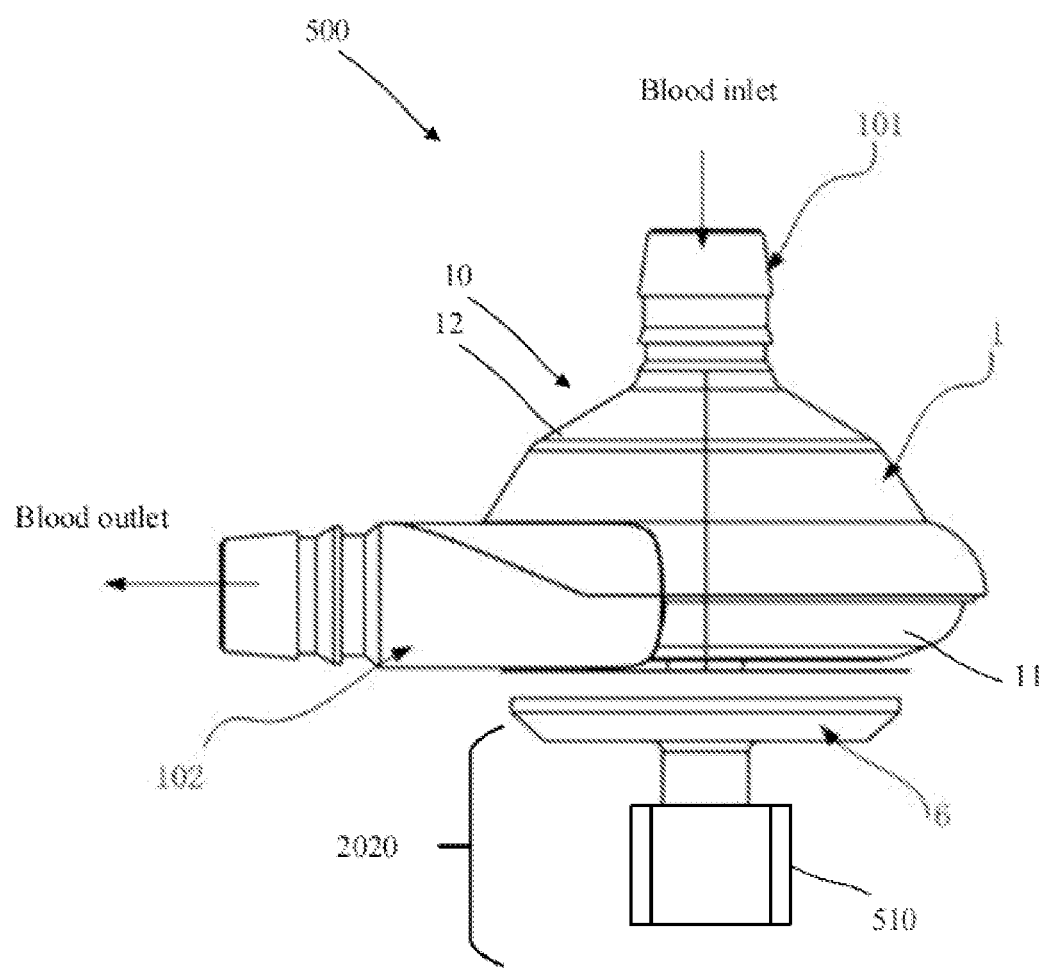
FIG. 5 schematically illustrates a side view of a portion of the structure of a pump including the volute pump head, according to an embodiment of the present disclosure.

The volute casing 1 may include a lower volute casing 11 and an upper volute casing 12. In some embodiments, as shown in FIG. 2, the shaft 103 may be a fixed shaft that is fixedly disposed at the lower volute casing 11. The shaft 103 may be disposed at a center location of the lower volute casing 11 and may be perpendicular to the center location of the lower volute casing 11. The shaft 103 may extend from the lower volute casing 11 toward the upper volute casing 12. For illustrative purposes, the shaft 103 is shown as having a cylindrical shape. It is understood that the shaft 103 may have any other suitable shapes, such as a rectangular prism shape. The magnetic structure 2 may have a hollow body. For illustrative purposes, the hollow body is shown as having a cylindrical shape. It is understood that the hollow body may have any suitable shape, such as a rectangular prism shape. The hollow body of the magnetic structure 2 may define a channel, through which the magnetic structure 2 may be sleeve-fit onto the exterior surface of the shaft 103. The conical impeller 3 and the magnetic structure 2 may be disposed between the lower volute casing 11 having the shaft 103 and the upper volute casing 12. The conical impeller 3 may be closer to the upper volute casing 12, and the magnetic structure 2 may be closer to the lower volute casing 11. The conical impeller 3 having an open structure 333 may be mounted (e.g., sleeve-fit) to an exterior surface of the body of the magnetic structure 2. The open structure 333 may be a cone-shaped structure including a cone-shaped surface 301, an upper opening 306, and a lower opening 316. A diameter of the lower opening 316 is larger than a diameter of the upper opening 306, as shown in FIG. 2. When the magnetic structure 2 rotates, the magnetic structure 2 may drive the conical impeller 3 mounted on the magnetic structure 2 to rotate. It should be noted that the rotation of the magnetic structure 2 may be driven by a suitable driving mechanism 2020, as shown in FIG. 5. For example, the driving mechanism 2020 may include a driving magnetic structure 6 having the same magnetism as the magnetic structure 2. The driving mechanism 2020 may also include an electric motor 510. The driving magnetic structure 6 may be mounted on a rotating shaft of the electric motor 510. The driving mechanism 2020 may be disposed adjacent the bottom of the lower volute casing 11 of the volute pump head 10. The electric motor 510 may drive the driving magnetic structure 6 to rotate. A magnetic field may exist between the driving magnetic structure 6 and the magnetic structure 2 disposed inside the volute casing 1. When the driving magnetic structure 6 rotates, the magnetic force may cause the magnetic structure 2 to rotate. The driving magnetic structure 6 mounted to the electric motor 510 may be a permanent magnet or an electromagnetic magnet. According to the embodiments of the present disclosure, a first gap may exist between the shaft 103 and the magnetic structure 2. When the magnetic structure 2 drives the conical impeller 3 to rotate, a portion of the blood may flow upwardly (e.g., in a direction from the lower volute casing 11 to the upper volute casing 12) through the first gap. The upward flow of the portion of the blood may exert an upward buoyant force on the conical impeller 3, which may lift the conical impeller 3 and the magnetic structure 2, to which the conical impeller 3 is mounted. Thus, the impeller 3 and the magnetic structure 2 may suspend in the blood. Because the conical impeller 3 suspends in the blood, the friction between the conical impeller 3 and other components of the pump head 10 (e.g., the casing 1) may be minimized or negligible, which may reduce the probability of blood clot formation when the blood flows through the impeller 3, and reducing the destruction of the blood cells.

According to the embodiments of the present disclosure, a plurality of vanes may be disposed at an exterior surface of the conical impeller 3. The vanes may include a plurality of first vanes 303 and second vanes 304 that are alternately arranged and spaced apart from one another. In the following descriptions, an example configuration having three first vanes and three second vanes is used to explain the disclosed technical solution. To better illustrate this embodiment, the first vanes are labelled as number 1 first vane 303a, number 2 first vane 303b, and number 3 first vane 303c. Similarly, the second vanes are labelled as number 1 second vane 304a, number 2 second vane 304b, and number 3 second vane 304c in FIGS. 2 and 3.

The first vanes and the second vanes may be alternately disposed on an exterior conical surface 301 of the conical impeller 3, and may be spaced apart from one another. A height (or heights) of the first vanes may be greater than a height (or heights) of the second vanes. The first vanes and the second vanes may be tilted toward a same side at a predetermined angle. For example, the three first vanes and the three second vanes may be tilted toward a same direction at an angle of about 30 degrees. Top portions of the first vanes may be connected together through a connecting structure 305. In some embodiments, the connecting structure 305 may have a bowl-shaped structure with a downward opening 401. For discussion purposes, in the following descriptions, the connecting structure 305 may be referred to as a first bowl-shaped structure 305. That is, the top portions of the number 1 first vane 303a, the number 2 first vane 303b, and the number 3 first vane 303c may be connected together through the first bowl-shaped structure 305 having a downward opening 401. The structural configurations of the first vanes and the second vanes are advantageous for thorough flushing, reducing blood clot formation, and reducing destruction of blood cells. By adopting a conical impeller having an open structure, as described herein, it is easier to exhaust air bubbles from the blood. The conical impeller with an open structure also effectively reduces heat generation, reduces blood clot formation, and reduces destruction of blood cells.

In some embodiments, the distances between a neighboring first vane and a neighboring second vane may be the same or may be different. For example, a first distance between the number 1 first vane 303a and the number 1 second vane 304a may be the same or different from a second distance between the number 1 first vane 303a and the number 3 second vane 304c.

Figure 4:
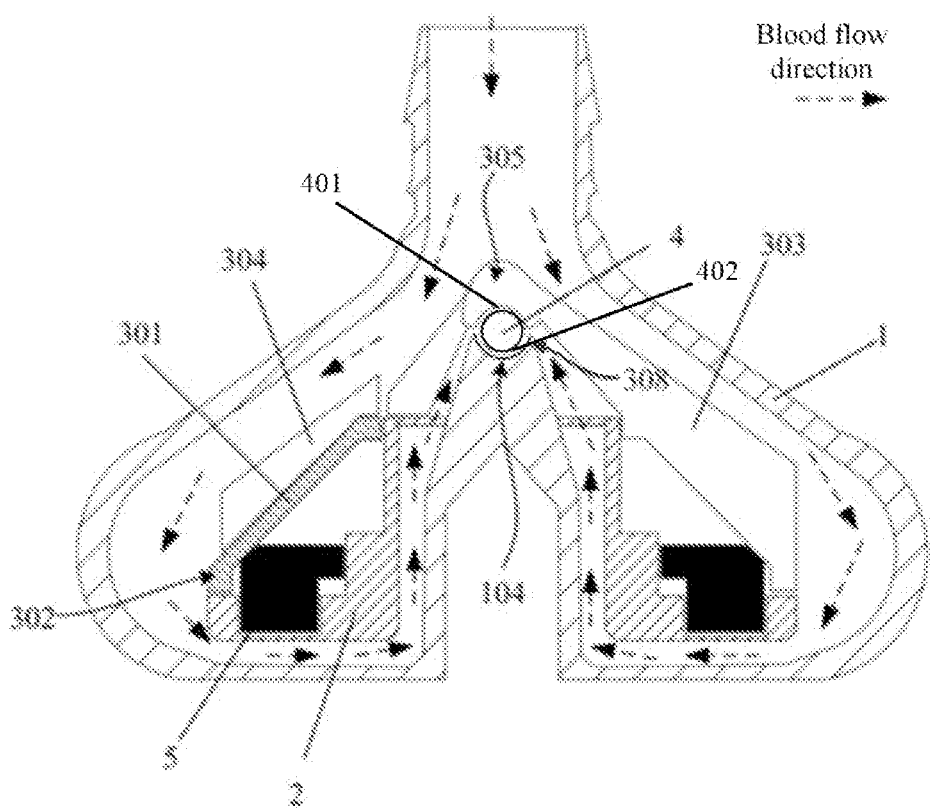
FIG. 4 schematically illustrates a cross-sectional view of the volute pump head configured for use in the artificial heart, according to an embodiment of the present disclosure.
Figure 7:
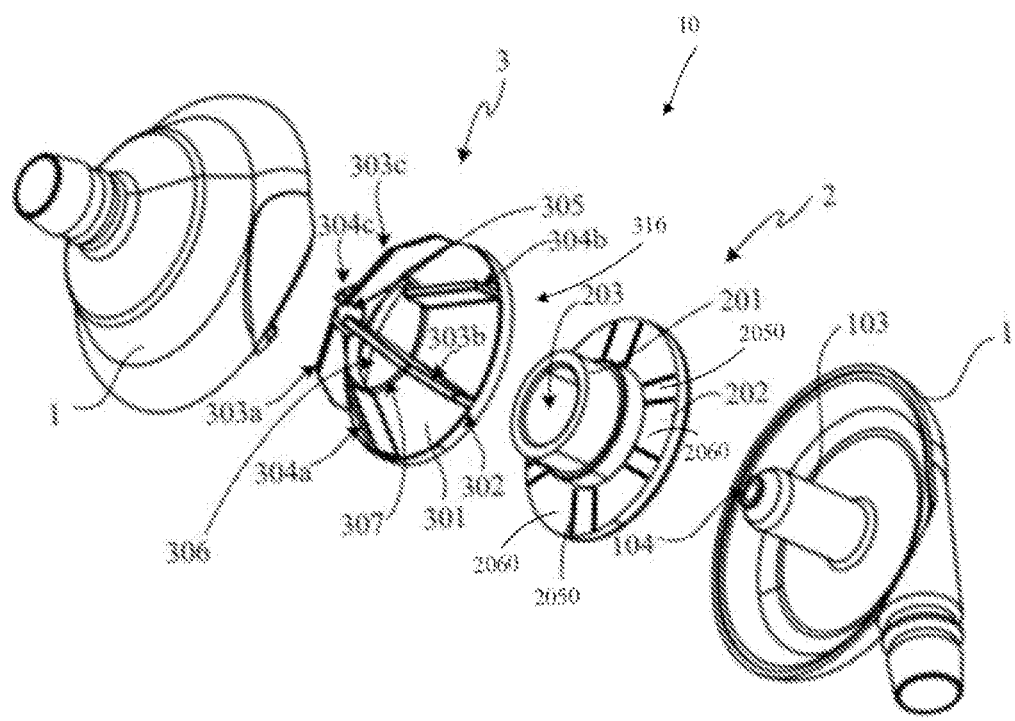
FIG. 7 schematically illustrates an exploded view of the volute pump head, according to another embodiment of the present disclosure.

In some embodiments of the present disclosure, the magnetic structure 2 may include a mounting shaft 201 having a hollow body. For illustrative purposes, the mounting shaft 201 is shown as having a cylindrical shape. It is understood that the mounting shaft 201 may have any other suitable shape, such as a rectangular prism shape. The mounting shaft 201 with the hollow body may sleeve-fit onto the shaft 103. An annular wheel structure 202 may be disposed or formed at a bottom portion of the mounting shaft 201. An outer diameter of the mounting shaft 201 may be the same as a diameter of the upper opening 306 at a top portion of the cone-shaped structure 333 of the conical impeller 3. The conical impeller 3 may be sleeve-fit onto the exterior surface of the mounting shaft 201 through the upper opening 306. A diameter of the annular wheel structure 202 may be the same as a diameter of the lower opening 316 at a bottom portion of the conical impeller 3. A plurality of mounting grooves 2021 may be provided at a surface of the annular wheel structure 202 and may be spaced apart from one another. Magnetic elements 5 may be mounted within the mounting grooves 2021, as shown in FIG. 4. The magnetic elements 5 may be any structure having or capable of generating a magnetism, such as permanent magnets, etc. The mounting grooves 2021 may have any suitable cross-sectional shape, such as square, rectangle, circle, oval, etc. Correspondingly, the magnetic elements 5 may have a suitable shape that matches with the cross-sectional shape of the mounting grooves 2021. The pump head 10 may be made of any suitable materials. For example, the pump head 10 may be made of a metal, a plastic, a carbon fiber, or a combination thereof. The mounting grooves 2021 may be depressions in the surface of the annular wheel structure 202, or may be through holes penetrating the surfaces of the annular wheel structure 202. In some embodiments, the mounting grooves 2021 may be provided at an upper surface (the surface facing the conical impeller 3) of the annular wheel structure 202, at a lower surface (the surface facing the lower volute casing 11) of the annular wheel structure 202, or at both upper surface and lower surface. In some embodiments, instead of having magnetic elements 5 disposed in the mounting grooves 2021, the entire structure of the annular wheel structure 202 may be formed by a plurality of segments, some of the segments may be magnetic elements, as shown in FIG. 7.

According to some embodiments of the present disclosure, as shown in FIG. 4, an end portion 104 of the shaft 103 may be depressed inwardly to form a second bowl-shaped structure 308 having an upward opening 402. A spherical structure 4 may be embedded or disposed between the first bowl-shaped structure 305 and the second bowl-shaped structure 308. That is, the spherical structure 4 may be disposed within a space formed by the first bowl-shaped structure 305 and the second bowl-shaped structure 308. A second gap may exist between the spherical structure 4 and the first bowl-shaped structure 305, and between the spherical structure 4 and the second bowl-shaped structure 308. When the magnetic structure 2 drives the conical impeller 3 to rotate, a portion of the blood may flow upwardly through the first gap, and a portion of the blood may fill in the second gap, which may cause the spherical structure 4 to suspend in the blood. Thus, the spherical structure 4 may not touch the shaft 103. This configuration reduces the friction between the spherical structure 4 and the end portion 104 of the shaft 103. Accordingly, the blood that is in touch with the spherical structure 4 may reduce the temperature of the spherical structure 4. In the meantime, this configuration may reduce the damage to the blood. Furthermore, the conical impeller 3 may be lifted, such that when rotating, the conical impeller 3 may suspend in the blood. Due to the suspension of the conical impeller 3 in the blood, and because the conical impeller 3 may not rub against the spherical structure 4, the temperature of the spherical structure 4 may be reduced. The reduction in the temperature of the spherical structure 4 may reduce the blood clot formation and the damage to the blood.

In some embodiments, the spherical structure 4 may be a ceramic ball. The ceramic ball 4 may function as a rotating bearing at the upper portion of the conical impeller 3, which renders the rotation of the conical impeller 3 smooth, thereby improving the efficiency of the blood flow. In the present disclosure, after the various components disposed inside the volute casing 1 are assembled, the shaft 103 may be inserted into a central channel (or bore) 203 of the mounting shaft 201 of the magnetic structure 2, such that the mounting shaft 201 may sleeve-fit onto the shaft 103. A diameter of the central channel 203 may be larger than a diameter of the shaft 103. Thus, a gap may exist between the magnetic structure 2 (e.g., the inner surface of the mounting shaft 201) and the shaft 103. The conical impeller 3 may be sleeve-fit onto the mounting shaft 201 to cover the magnetic structure 2. The spherical structure 4 disposed at the end portion 104 of shaft 103 may be embedded in a depressed groove formed between and by the first bowl-shaped structure 305 having a downward opening 401 and the second bowl-shaped structure 308 having an upward opening 402. An exterior edge of the mounting shaft 201 may be flush with an edge 307 of the upper opening 306 at the top portion of the conical impeller 3. An exterior edge of the annular wheel structure 202 may be flush with an edge 302 of a bottom portion of the conical impeller 3. That is, the mounting shaft 201 may extend into the upper opening 306 of the conical impeller 3, and may be coupled with the edge 307 of the upper opening 306. The edge 302 of the conical impeller 3 may be coupled with the exterior edge of the annular wheel structure 202.

As shown in FIG. 4 and FIG. 5, when the electric motor 510 drives the driving magnetic structure 6 located at the bottom of the volute casing 1 to rotate, the driving magnetic structure 6 may cause the magnetic structure 2 to rotate through the magnetic field between the driving magnetic structure 6 and the magnetic structure 2, thereby causing the conical impeller 3 mounted on the magnetic structure 2 to rotate. The centrifugal force generated by the rotation of the conical impeller 3 may cause the blood to flow into the chamber of the volute casing 1 through the blood inlet 101. The blood may flow out of the chamber of the volute casing 1 through the blood outlet 102 due to the centrifugal force generated by the rotation of the conical impeller 3. Thus, a pump 500 (shown in FIG. 5) including the pump head 10 may be referred to as a centrifugal blood pump.

During an operation, the blood may fill the chamber of the volute casing 1. A major portion of the blood may undergo a centrifugal movement due to the rotation of the conical impeller 3, and may flow out of the chamber of the volute casing 1 through the blood outlet 102. A small portion of the blood may flow to the bottom portion of the volute casing 1, and may move upwardly through the first gap between the shaft 103 and the magnetic structure 2. The conical impeller 3 may be lifted upwardly away from the spherical structure 4 (which may be a ceramic ball) through the centrifugal force and a mechanical force. The mechanical force may be generated by the spherical structure 4 that is disposed at the end portion 104 of the shaft 103. The mechanical force causes the conical impeller 3 to suspend in the blood, thereby reducing the load and the friction on the spherical structure 4. In the present disclosure, the spherical structure 4 may not rub against the first bowl-shaped structure 305 having a downward opening 401 included in the conical impeller 3. As a result, the temperature of the spherical structure 4 can be reduced. The reduction in temperature can significantly reduce the formation of blood clots and the damage to the blood.

The volume of the volute pump head 10 configured for an artificial heart according to the present disclosure is small. The centrifugal force generated by the rotation of the conical impeller 3 may cause a major portion of the blood flow to enter the chamber of the volute casing 1 through the blood inlet 101 and exit the chamber through the blood outlet 102. A small portion of the blood may flow along an additional path inside the chamber, as described above. The small portion of the blood may protect the internal components by lifting the conical impeller 3 and the spherical structure 4, thereby reducing the blood clot formation, reducing heat generation by the components disposed inside the volute casing 1, and functioning as a lubrication to the components.

The volute pump head 10 configured for use in an artificial heart according to the present disclosure can be used along with a dynamic pump for the artificial heart. To address the deficiencies and disadvantages of the conventional technologies, the systems and devices of the present disclosure can provide a reasonable extracorporeal blood circulation environment. The technical solutions provided by the present disclosure can be used in portable emergency rescue devices such as ECMO devices. The volume of the pump head of the present disclosure is small, which can effectively reduce the precharge amount. The disclosed pump head includes a conical impeller having an open, cone-shaped structure, which makes it easier to exhaust gas bubbles from the blood. The heights and the tilting design of the first vanes and the second vanes are configured to be advantageous for thorough flushing and for effectively reducing blood clot formation and destruction of blood cells. The design of the conical impeller and the shaft disposed inside the volute casing can effectively reduce heat generation, reduce the blood clot formation, and avoid destruction of the blood cells.

According to a second aspect of the present disclosure, as shown in FIG. 5, the present disclosure also provides the pump 500, which may be configured for an artificial heart (also referred to as an artificial heart pump 500, a dynamic pump 500, or a centrifugal blood pump 500). The pump 500 for the artificial heart may include the volute pump head 10 according to any of the above embodiments or technical solutions described herein.

As shown in FIG. 5, the pump 500 may include the driving magnetic structure 6 provided adjacent a lower portion of the volute pump head 10. For example, the driving magnetic structure 6 may be spaced apart from the lower volute casing 11 with a gap. The driving magnetic structure 6 may be fixedly mounted to the electric motor 510. When the electric motor 510 rotates, the driving magnetic structure 6 mounted on the electric motor 510 may be driven to rotate. The magnetic structure 6 may generate a magnetic field, which in turn may apply a magnetic force on the magnetic structure 2 disposed inside the volute casing 1 of the pump head 10. The magnetic force may drive the magnetic structure 2 to rotate. The driving mechanism 2020 may include driving devices other than the electric motor 510, which is not limited by the present disclosure.

Figure 6:
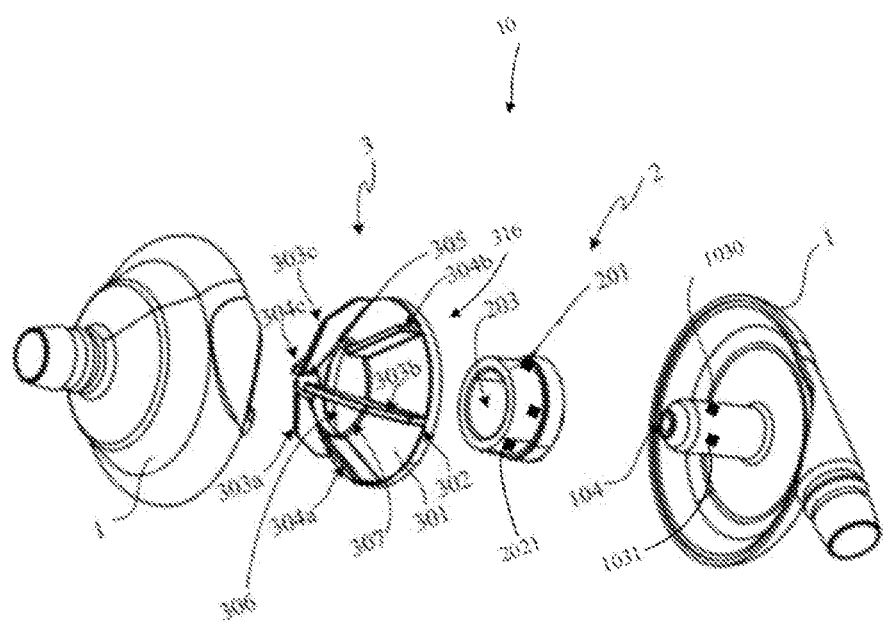
FIG. 6 schematically illustrates an exploded view of the volute pump head, according to another embodiment of the present disclosure.

FIG. 6 illustrate an exploded view of the volute pump head 10, according to another embodiment of the present disclosure. This embodiment includes structures and elements similar to those shown in FIG. 2. The descriptions of the similar or the same structures and elements and their functions may refer to the above descriptions. As shown in FIG. 6, the shaft 103 included in the embodiment shown in FIG. 2 is replaced by a rotating shaft 1030. Although not shown in FIG. 6, the rotating shaft 1030 may be directly coupled with a rotating shaft of the electric motor 510 of the driving mechanism 2020 shown in FIG. 5, and the driving magnetic structure 6 may be eliminated. The rotating shaft 1030 may include a plurality of magnetic elements 1031 distributed along the exterior surface of the shaft 103. Correspondingly, the mounting shaft 201 of the magnetic structure 2 may include a plurality of magnetic elements 2021 distributed along the inner surface and/or the outer surface of the mounting shaft 201. In the magnetic structure 2, the annular wheel structure 202 may be eliminated. When the magnetic structure 2 is sleeve-fit onto the rotating shaft 103 with a gap between the mounting shaft 201 and the rotating shaft 103, the magnetic elements 2021 on the mounting shaft 201 may correspond to the magnetic elements 1031 on the rotating shaft 103. When the rotating shaft 1030 is driven by the electric motor of the driving mechanism 2020 to rotate, the magnetic force between the magnetic elements 1031 and the magnetic elements 2021 mounted on the mounting structure 201 may cause the magnetic structure 2 to rotate. When the volute pump head 10 is in the embodiment shown in FIG. 6, the pump 500 may include the volute pump head 10 as shown in FIG. 6 and the driving mechanism 2020 including the electric motor 510 but not including the driving magnetic structure 6.

FIG. 7 is an exploded view of the volute pump head 10 according to another embodiment of the present disclosure. This embodiment includes structures and elements similar to those shown in FIG. 2. The descriptions of the similar or the same structures and elements and their functions may refer to the above descriptions. As shown in FIG. 7, instead of disposing magnetic elements 2021 in grooves, the annular wheel structure 202 is formed by a plurality of magnetic segments 2050 and a plurality of non-magnetic segments 2060 that are alternately distributed and coupled together. The magnetic segments 2050 may magnetically couple with the driving magnetic structure 6 shown in FIG. 5. For example, the driving magnetic structure 6 may include a plurality of magnetic elements corresponding to the magnetic segments 2050. When the magnetic structure 6 is driven by the electric motor 510 to rotate, the rotation may cause the annular wheel structure 202 to rotate due to the magnetic force between the magnetic structure 6 and the magnetic segments 2050. The other structures and elements are the same as those described above in connection with FIG. 2 and FIG. 5. When the volute pump head 10 is in the embodiment shown in FIG. 7, the pump 500 may include the volute pump head 10 shown in FIG. 7 and the driving mechanism 2020 (including the driving magnetic structure 6 and the electric motor 510) shown in FIG. 5.

Figure 8:
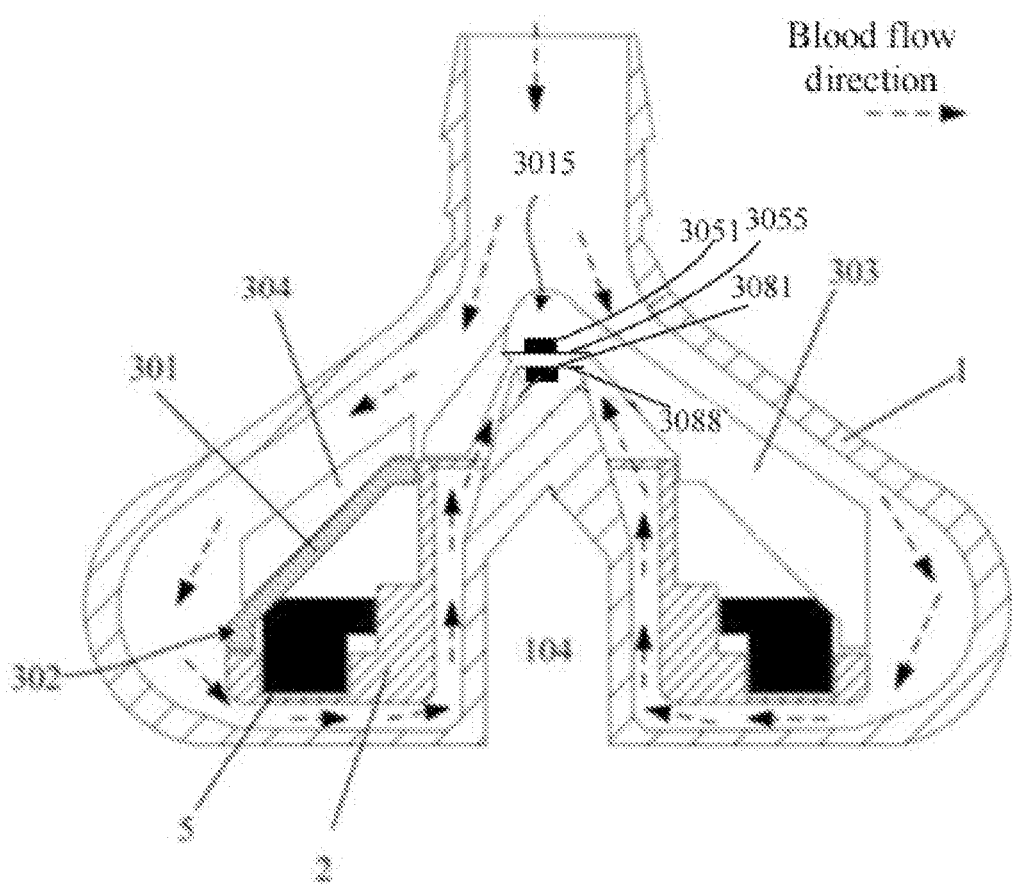
FIG. 8 schematically illustrates a cross-sectional view of the volute pump head, according to another embodiment of the present disclosure.

FIG. 8 schematically illustrates a cross-sectional view of the volute pump head 10 configured for use in the artificial heart, according to another embodiment of the present disclosure. This embodiment includes structures and elements similar to those shown in FIG. 4. In this embodiment, the end portion 104 may not have a bowl-shaped structure 308 shown in FIG. 4. Instead, the end portion 104 of the shaft 103 may have a first flat surface 3088. A first magnetic element 3081 may be disposed at the first flat surface 3088. Correspondingly, the conical impeller 3 may not have a bowl-shaped structure 305. Instead, the conical impeller 3 may have an upper structure 3015 with a second flat surface 3055 facing the first flat surface 3088 of the end portion 104 of the shaft 103. A second magnetic element 3051 may be disposed at the second flat surface 3055 facing the first magnetic element 3081. The second magnetic element 3051 may be magnetically coupled with the first magnetic element 3081. Although one magnetic element is shown as being disposed at each of the first and second flat surfaces, it is understood that in some embodiments, a plurality of magnetic elements may be disposed at each flat surface 3088 or 3055. In some embodiments, the magnetic elements 3051 and 3081 may provide a repulsive magnetic force, which may push the upper structure 3015 away from the end portion 104 to maintain a gap between the second flat surface 3055 and the first flat surface 3088. Thus, during operation, the rotating conical impeller 3 may not contact the end portion 104 of the shaft 103, thereby eliminating or reducing the friction between the conical impeller 3 and the shaft 103. In some embodiments, the magnetic elements 3051 and 3081 may provide an attractive magnetic force. During operation, the upward flowing blood may push the conical impeller 3 away from the end portion 104 of the shaft 103, and the attractive magnetic force between the magnetic elements 3051 and 3081 may pull the conical impeller 3 toward the end portion 104. The magnetic elements 3051 and 3081 may be configured with a suitable attractive magnetic force such that the conical impeller 3 suspends in the blood during an operation, with a gap between the second flat surface 3055 and the first flat surface 3088, thereby eliminating or reducing the friction between the conical impeller 3 and the shaft 103.

Figure 9:
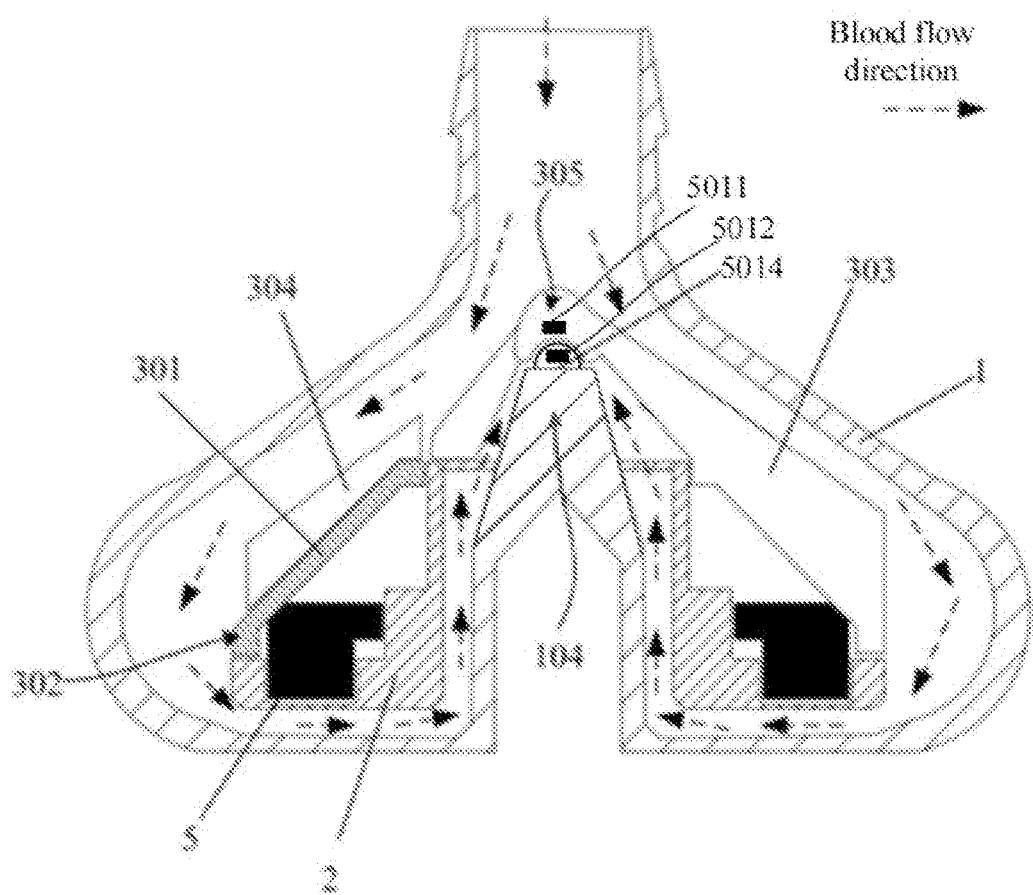
FIG. 9 schematically illustrates a cross-sectional view of the volute pump head, according to another embodiment of the present disclosure.

FIG. 9 schematically illustrates a cross-sectional view of the volute pump head 10 configured for use in the artificial heart, according to another embodiment of the present disclosure. This embodiment includes structures and elements similar to those shown in FIG. 4. In this embodiment, the end portion 104 may include a spherical structure 5014 disposed a tip portion of the end portion 104. The bowl-shaped structure 305 of the conical impeller 3 may have a curved surface corresponding to the spherical structure 5014 of the end portion 104. A gap may exist between the curved surface of the bowl-shaped structure 305 and the spherical structure 5014. A magnetic element 5011 may be disposed at the curved surface of the bowl-shaped structure 305 or behind the curved surface of the bowl-shaped structure 305. A corresponding magnetic element 5012 may be disposed at the exterior surface of the spherical structure 5014 of the end portion 104 of the shaft 103, or behind the surface of the spherical structure 5014. The magnetic elements 5011 and 5012 may be magnetically coupled with one another. In some embodiments, the magnetic elements 5011 and 5012 may generate a repulsive magnetic force, which may push the conical impeller 3 away from the end portion 104. Thus, during an operation, the conical impeller 3 may suspend in the blood with a gap between the bowl-shaped structure 305 and the spherical structure 5014 of the end portion 104 of the shaft 103. The gap may eliminate or reduce the friction between the conical impeller 3 and the shaft 103 during an operation.

In some embodiments, the magnetic elements 5011 and 5012 may be suitably configured to generate an attractive magnetic force, which may pull the conical impeller 3 toward the end portion 104. During an operation, the upward flow of the blood may apply a force on the conical impeller 3 to push the conical impeller 3 upwardly, away from the end portion 104. The attractive magnetic force may be suitably designed to counter a portion of the upward pushing force generated by the upward flow of the blood, thereby maintaining a suitable gap between the spherical structure 5014 and the bowl-shaped structure 305 of the conical impeller 3. The gap may eliminate or reduce the friction between the conical impeller 3 and the shaft 103 during an operation.

Although the configurations of the structures facing each other for the conical impeller 3 and the end portion 104 shown in FIGS. 8 and 9 are each illustrated based on the embodiment shown in FIGS. 2 and 4, it is understood that the same configurations of the structures facing each other for the conical impeller 3 and the end portion 104 may be applicable to the embodiments shown in FIG. 6 and FIG. 7.

Compared with the conventional technologies, the advantages provided by the pump for the artificial heart according to the present disclosure may be similar to the advantages provided by the pump head according to any of the technical solutions described herein, which are not repeated.

According to a third aspect of the present disclosure, the present disclosure also provides an ECMO device. The ECMO device may include a pump (or a dynamic pump, a centrifugal blood pump) according to any of the technical solutions described herein. FIG. 10 schematically illustrates an ECMO device 1000 including the pump 500 that includes the disclosed volute pump head 10, according to an embodiment of the present disclosure. As shown in FIG. 10, the ECMO device 1000 include the pump 500 and an oxygenator 600. The pump 500 and the oxygenator 600 may be fluidly coupled with one another through one or more tubings (or conduits) 1011. The pump 500 and the oxygenator 600 may be fluidly coupled with the heart of a patient 700 through tubings (or conduits) 1011. The oxygenator 600 may be configured to exchange oxygen and carbon dioxide with the blood, functioning as an artificial lung. That is, carbon dioxide may be exchanged out of the blood and oxygen may be exchanged into the blood. As shown by the arrows (indicating the blood flowing direction) in FIG. 10, the blood flowing out of the patient is pumped by the pump 500 to flow through the oxygenator 600, in which the oxygen is exchanged into the blood, and carbon dioxide is exchanged out of the blood. The blood output from the oxygenator 600 continues to flow into the heart of the patient. The ECMO device 1000 may also include a controller 800. The controller 800 may include a suitable processor and/or a non-transitory computer-readable storage medium. The non-transitory computer-readable storage medium may be configured to store data, including computer-executable software or program codes or instructions. The processor may include any suitable data processing devices, such as a central processing unit ("CPUs"). The controller 800 may be communicatively coupled with the pump 500 and the oxygenator 600, and may control the operations of the pump 500 and the oxygenator 600. For example, the controller 800 may control the rotating speed of the driving mechanism 2020 to control the rotating speed of the conical impeller 3, thereby controlling the gap between the conical impeller 3 and the end portion 104, i.e., to control the suspension of the conical impeller 3 in order to minimize the friction and maximize the blood pumping efficiency.

Compared with the conventional technologies, the advantages of the ECMO device of the present disclosure may be similar to the advantages of the pump head configured for use in an artificial heart, which are not repeated.

In view of the descriptions and practice of the present disclosure, other embodiments of the present disclosure may be easily conceived and understood by a person having ordinary skills in the art. The descriptions and the embodiments are merely illustrative. The true scope and principles of the present disclosure are defined by the following claims.

What is claimed is:

1. A pump head comprising:
   a casing comprising an upper portion, a lower portion, a blood inlet disposed at the upper portion to receive blood and a blood outlet disposed at the lower portion to allow the blood to flow out of the casing;
   a fixed shaft disposed in the lower portion of the casing;
   a hollow magnetic structure, the hollow magnetic structure comprising a hollow mounting shaft mounted onto the fixed shaft and driving an impeller to rotate; and
   the impeller having an open structure and mounted to an exterior surface of the hollow magnetic structure through an opening provided at the open structure;
   wherein a first gap is provided between the fixed shaft and the hollow magnetic structure;
   when the hollow magnetic structure drives the impeller to rotate, a portion of the blood flows from a bottom of the casing upwardly through the first gap toward a top of the casing to cause the impeller to suspend in the blood;
   the impeller comprises a plurality of vanes disposed at an exterior surface of the open structure, the plurality of vanes comprising a plurality of first vanes and a plurality of second vanes,
   top portions of the first vanes are connected through a first bowl-shaped structure having a downward opening,
   the fixed shaft comprises a second bowl-shaped structure having an upward opening at an end of the fixed shaft,
   a spherical structure is disposed between the first bowl-shaped structure and the second bowl-shaped structure, and
   when the hollow magnetic structure drives the impeller to rotate, a second gap is provided between the spherical structure and the first bowl-shaped structure and the second bowl-shaped structure, the second gap being filled with the blood.

2. The pump head of claim 1, wherein
   the first vanes and the second vanes are configured to tilt toward a same side at a predetermined angle.

3. The pump head of claim 2, wherein heights of the first vanes are greater than heights of the second vanes.

4. The pump head of claim 1, wherein
   an annular wheel structure is disposed at a bottom portion of the hollow mounting shaft, and
   a diameter of the annular wheel structure is substantially the same as a diameter of an opening at a bottom portion of the open structure of the impeller.

5. The pump head of claim 4, wherein
   the annular wheel structure comprises a plurality of mounting grooves disposed at a surface of the annular wheel structure, the mounting grooves being spaced apart, and
   a plurality of magnetic elements are mounted in the mounting grooves.

6. The pump head of claim 4, wherein an outer diameter of the hollow mounting shaft is substantially the same as a diameter of an opening at a top portion of the open structure of the impeller.

7. The pump head of claim 1, wherein the spherical structure is a ceramic ball.

8. A pump head comprising:
   a casing comprising an upper portion, a lower portion, a blood inlet disposed at the upper portion to receive blood and a blood outlet disposed at the lower portion to allow the blood to flow out of the casing;
   a fixed shaft disposed in the lower portion of the casing;
   a hollow magnetic structure, the hollow magnetic structuring comprising a hollow mounting shaft mounted onto the fixed shaft and driving an impeller to rotate; and
   the impeller having an open structure and mounted to an exterior surface of the hollow magnetic structure through an opening provided at the open structure;
   wherein a first gap is provided between the fixed shaft and the hollow magnetic structure; when the hollow magnetic structure drives the impeller to rotate, a portion of the blood flows from a bottom of the casing upwardly through the first gap toward a top of the casing to cause the impeller to suspend in the blood;
   the fixed shaft comprises an end portion having a first flat surface and a first magnetic element disposed at the first flat surface, and
   the impeller comprises an upper structure having a second flat surface and a second magnetic element disposed at the second flat surface, the second magnetic element magnetically coupled with the first magnetic element.

9. A pump head comprising:
   a casing comprising an upper portion, a lower portion, a blood inlet disposed at the upper portion to receive blood and a blood outlet disposed at the lower portion to allow the blood to flow out of the casing;
   a fixed shaft disposed in the lower portion of the casing;
   a hollow magnetic structure, the hollow magnetic structure comprising a hollow mounting shaft mounted onto the fixed shaft and driving an impeller to rotate; and
   the impeller having an open structure and mounted to an exterior surface of the hollow magnetic structure through an opening provided at the open structure;
   wherein a first gap is provided between the fixed shaft and the hollow magnetic structure; when the hollow magnetic structure drives the impeller to rotate, a portion of the blood flows from a bottom of the casing upwardly through the first gap toward a top of the casing to cause the impeller to suspend in the blood;
   the fixed shaft comprises an end portion having a spherical structure comprising a first magnetic element, and
   the impeller comprises a bowl-shaped structure facing the spherical structure, the bowl-shaped structure comprising a second magnetic element, the second magnetic element being magnetically coupled with the first magnetic element.

* * * * *